US012788259B2

(12) United States Patent
McGrath et al.

(10) Patent No.: US 12,788,259 B2
(45) Date of Patent: Nov. 10, 2026

(54) DEVICE AND SYSTEM FOR DETECTING HEART RHYTHM ABNORMALITIES

(71) Applicant: NATIONAL UNIVERSITY OF IRELAND, GALWAY, Galway (IE)

(72) Inventors: Oisín McGrath, Galway (IE); Eddie McDaid, Galway (IE); Patrick Conway, Galway (IE); Mark Bruzzi, Galway (IE); Gurkan Dogan, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 655 days.

(21) Appl. No.: 18/027,862

(22) PCT Filed: Sep. 22, 2021

(86) PCT No.: PCT/EP2021/076129
§ 371 (c)(1),
(2) Date: Mar. 22, 2023

(87) PCT Pub. No.: WO2022/063864
PCT Pub. Date: Mar. 31, 2022

(65) Prior Publication Data
US 2023/0346231 A1 Nov. 2, 2023

(30) Foreign Application Priority Data
Sep. 23, 2020 (EP) .................................... 20197926

(51) Int. Cl.
*A61B 5/0205* (2006.01)
*A61B 5/024* (2006.01)
(Continued)

(52) U.S. Cl.
CPC .......... *A61B 5/0205* (2013.01); *A61B 5/1118* (2013.01); *A61B 5/14551* (2013.01);
(Continued)

(58) Field of Classification Search
CPC . A61B 5/0205; A61B 5/1118; A61B 5/14551; A61B 5/02438; A61B 5/0245
See application file for complete search history.

(56) References Cited

U.S. PATENT DOCUMENTS 10,154,460 B1 12/2018 Miller et al.
11,026,628 B1 * 6/2021 Bruinsma .............. A61B 5/681
(Continued)

FOREIGN PATENT DOCUMENTS

CN 106725393 A 5/2017
CN 108113647 A 6/2018
(Continued)

OTHER PUBLICATIONS

International Preliminary Report on Patentability for PCT App. PCT/EP2021/076129 dated Mar. 28, 2023 (21 pages).
(Continued)

*Primary Examiner* — Amanda L Steinberg
(74) *Attorney, Agent, or Firm* — Foley & Lardner LLP

(57) ABSTRACT

A wearable device for detecting heart rhythm abnormalities, comprising: a sensor unit comprising at least one pulse oximeter; a processor unit; a memory unit; and a power unit comprising a battery and configured to disseminate battery power amongst various components of the wearable device; wherein, the at least one pulse oximeter is configured to measure optically a bloodstream at a sampling rate and output first data; wherein, the processor unit is configured to process the first data and determine a time for the processed first data to be automatically recorded in the memory unit; wherein, the processor unit is configured to dynamically adjust the sampling rate of the at least one pulse oximeter based on a predetermined event; and wherein, the processor unit is configured to control the power unit in such a way that the sampling rate is dynamically adjusted through applying varying power levels to the sensor unit and consequently the
(Continued)

wearable device is operable to enable a duration up to 90 days for a single continuous recording of the processed first data.

11 Claims, 7 Drawing Sheets

(51) Int. Cl.
*A61B 5/0245* (2006.01)
*A61B 5/11* (2006.01)
*A61B 5/1455* (2006.01)

(52) U.S. Cl.
CPC ......... *A61B 5/02438* (2013.01); *A61B 5/0245* (2013.01); *A61B 2562/0219* (2013.01)

(56) References Cited

U.S. PATENT DOCUMENTS

| | | | | |
|---|---|---|---|---|
| 2004/0147707 | A1 | 7/2004 | Arendoski | |
| 2013/0345569 | A1 | 12/2013 | Mestha et al. | |
| 2015/0359491 | A1 | 12/2015 | Luna et al. | |
| 2016/0120433 | A1* | 5/2016 | Hughes | G16H 40/63 600/483 |
| 2016/0135692 | A1* | 5/2016 | Lisogurski | A61B 5/14551 600/324 |
| 2016/0274726 | A1 | 9/2016 | Chung et al. | |
| 2017/0209055 | A1* | 7/2017 | Pantelopoulos | A61B 5/7203 |
| 2018/0279891 | A1* | 10/2018 | Miao | A61B 5/02416 |
| 2019/0104951 | A1* | 4/2019 | Valys | G16H 50/20 |
| 2019/0133829 | A1 | 5/2019 | Hofbauer et al. | |
| 2019/0178980 | A1* | 6/2019 | Zhang | A61B 5/7267 |
| 2019/0196411 | A1 | 6/2019 | Yuen | |
| 2019/0336083 | A1* | 11/2019 | Gill | A61B 5/352 |
| 2020/0100693 | A1 | 4/2020 | Velo | |
| 2020/0312453 | A1* | 10/2020 | Räisänen | G16H 50/20 |

FOREIGN PATENT DOCUMENTS

| | | | |
|---|---|---|---|
| CN | 109856699 | A | 6/2019 |
| JP | 2015-016216 | A | 1/2015 |
| JP | 2017-209413 | A | 11/2017 |
| JP | 2019-051011 | A | 4/2019 |
| JP | 2020-060872 | A | 4/2020 |
| WO | WO2012/140559 | A1 | 10/2012 |
| WO | WO2016/210334 | A1 | 12/2016 |
| WO | WO2020/104986 | A2 | 5/2020 |

OTHER PUBLICATIONS

International Search Report and Written Opinion cited in the PCT Application No. PCT/EP2021/076129.

JP Office Action for Application No. 2023-518210 mailing date Jul. 29, 2025, 14 pages with English translation.

CN Office Action on CN Appl. No. 202180078247.3 dated Apr. 22, 2026 (18 pages).

JP Office Action on JP Appl. No. 2023-518210 dated Dec. 9, 2025 (12 pages).

* cited by examiner

DEVICE AND SYSTEM FOR DETECTING HEART RHYTHM ABNORMALITIES

CROSS-REFERENCE TO RELATED APPLICATIONS

This application claims the benefit of priority to International Application No. PCT/EP2021/076129, filed on Sep. 22, 2021, which claims the benefit of European Patent Application No. 20197926.7, filed Sep. 23, 2020, all of which are hereby incorporated by reference in their entirety.

FIELD OF THE INVENTION

The present invention relates to methods and systems for long-term monitoring of heart rhythm and the detection of heart rhythm abnormalities, in particular for reliable and accurate detection of intermittent/asymptomatic atrial fibrillation.

BACKGROUND TO THE INVENTION

Atrial fibrillation (AFib) is the most common heart rhythm irregularity, affecting over 33.5 million individuals globally, and is the source of significant preventable annual healthcare costs worldwide. The pathology causes a decrease in the efficiency of the heart's ability to pump blood, potentially resulting in clot formation. AFib is responsible for 50% of all fatal ischemic strokes, and sufferers are at a 5 times higher risk of stroke. Silent AFib constitutes up to 60% of all AFib and greatly extends the time to diagnosis due to the intermittent and asymptomatic nature of the AFib events. Early detection of this form of AFib presents challenges in the form of continuous recording duration, which are hampered by monitoring device convenience, type, environment of use, and wearer-compliance.

The current gold standard approach for monitoring and recording heart waveforms non-invasively is electrocardiography (ECG). ECG records the electrical activity of the heart and stores the waveform, which is typically printed out to a screen or document. Conventional wearable ECG monitors are not an ideal solution for monitoring periods which span more than a small number of days, and they are generally unable to record the heart waveform reliably during excessive motion, or while wet. In addition, ECG monitors tend to be large, inconvenient, and power hungry, or require wearer interaction to function.

Pulse oximetry is an alternative approach to measuring heart activity, but its utility has thus far been limited to measuring pulse rate and blood oxygenation levels rather than full heart rhythm. Pulse oximetry operates by sampling the bloodstream with light pulses and measuring property changes (e.g., intensity) of light pulses passing through or reflecting from the bloodstream. For example, by measuring intensity changes of light with varying wavelengths, the haemoglobin/deoxyhaemoglobin gradient change representing blood volume in a vessel at any given point in time can be monitored/measured. This data can provide in-depth information on cardiovascular functionality with the application of advanced processing methods.

Pulse oximeter sensors are featured in many sports wearables such as sports trackers or smartwatches today. These platforms typically offer a host of other features such as GPS, fitness applications, Bluetooth, Wi-Fi, screen display and more in order to compete within the consumer market. The pulse oximeter sensors incorporated into these devices are low performance, and are incapable of providing the data that cardiologists need in order to detect waveform abnormalities which may be indicative of AFib. For example, existing pulse oximetry-based devices typically have a low sampling/polling frequency in the range of 5 Hz to 215 Hz. A poor temporal resolution, resulting from a low sampling frequency, makes such devices unable to resolve certain temporal features of a heart rhythm waveform that are important for determining AFib. As such, the output waveform readings from such devices are of lower quality and lower reliability. In addition to this, the necessity of hosting a wide range of functionality to maintain a competitive edge within the consumer market limits battery life, curtailing a key feature necessary to reliably monitor for infrequently occurring heart rhythm abnormalities over long durations.

Due to specific difficulties in identifying silent AFib, patients can wait years to obtain a diagnosis using current wearable heart rhythm monitoring methods such as Holter monitor and patch ECGs, leaving sufferers at significant risk of stroke, and leaving health systems exposed to significant cost increases. The intermittent nature of silent AFib means that it is difficult to detect accurately and reliably without a system which can monitor continuously in everyday settings for time periods extending into weeks and months.

SUMMARY OF THE INVENTION

Hence, it is the objective of this disclosure to provide a method and a system that are based either on solely pulse oximetry or on a combination of pulse oximetry and ECG, and are dedicated to long-term continuous heart rhythm monitoring. The proposed method and system are capable of reliably detecting heart rhythm abnormalities e.g., heart arrhythmia while obviating or mitigating most or all of the aforementioned problems associated with existing monitoring devices.

In accordance with a first aspect of the present invention, there is provided a wearable device for detecting heart rhythm abnormalities, comprising: a sensor unit comprising at least one pulse oximeter; a processor unit; a memory unit; and a power unit comprising a battery and configured to disseminate battery power amongst various components of the wearable device; wherein, the at least one pulse oximeter is configured to measure optically a bloodstream at a sampling rate and output first data; wherein, the processor unit is configured to process the first data and determine a time for the processed first data to be automatically recorded in the memory unit; wherein, the processor unit is configured to dynamically adjust the sampling rate of the at least one pulse oximeter based on a predetermined event; and wherein, the processor unit is configured to control the power unit in such a way that the sampling rate is dynamically adjusted through applying varying power levels to the sensor unit and consequently the wearable device is operable to enable a duration up to 90 days for a single continuous recording of the processed first data.

In accordance with a second aspect of the present invention, there is provided a charging device configured for charging and transferring data from a wearable device according to the first aspect, comprising: an AC-DC Converter configured to convert the mains AC supply to DC power; a data transfer and charging unit comprising a data transfer and charging circuitry; and at least one charging bay recessed from a top surface of the charging device and configured to accommodate the wearable device; wherein, the at least one charging bay comprises one or more metal contact points configured to establish complementary connections to the wearable device, further wherein each metal contact point is connected to one contact of the data transfer and charging circuitry.

In accordance with a third aspect of the present invention, there is provided a system for detecting heart rhythm abnormalities, comprising a wearable device according to the first aspect of the present invention, a charging device as according to the second aspect of the present invention, a computing device in connection with both the charging device and the internet; and an online analysis platform accessible by the computer device and configured to process and analyse electrical data transferred from the wearable device in order to determine heart rhythm abnormalities; wherein upon detecting a satisfactory heartbeat signal, the wearable device automatically begins recording of heart data obtained by optically measuring a bloodstream at a sampling rate; wherein the wearable device is operable to dynamically adjust the sampling rate based on a predetermined event.

In accordance with a fourth aspect of the present invention, there is provided a method for heart rhythm monitoring, comprising: measuring optically a bloodstream optically at a sampling rate and outputting measured data using at least one pulse oximeter; processing the measured data and determining a time for the processed data to be automatically recorded using a processor unit; adjusting dynamically the sampling rate of the at least one pulse oximeter based on a predetermined event.

In accordance with a fifth aspect of the present invention, there is provided a method for detecting heart rhythm abnormalities, comprising: measuring optically a bloodstream at a sampling rate and outputting first data using at least one pulse oximeter; measuring heart rhythm activity using an ECG sensor having one or more pairs of dry electrodes, each pair of dry electrodes generating a voltage signal; recording, from a first time instance, the first data measured by the at least one pulse oximeter; analysing the first data to determine presence of any irregularity in peak-to-peak pulse timings; recording, from a second time instance, second data comprising one or more voltage signals; and transmitting at least part of the second data via a mobile network without affecting the recording of the first data; wherein the first time instance is when one or more voltage signals exceeds a voltage threshold; wherein the second time instance is when irregularity in peak-to-peak pulse timings is identified in the first data.

DETAILED DESCRIPTION

Embodiments of the present invention will now be described by way of example only and with reference to the accompanying drawings, in which.

Figure 6:
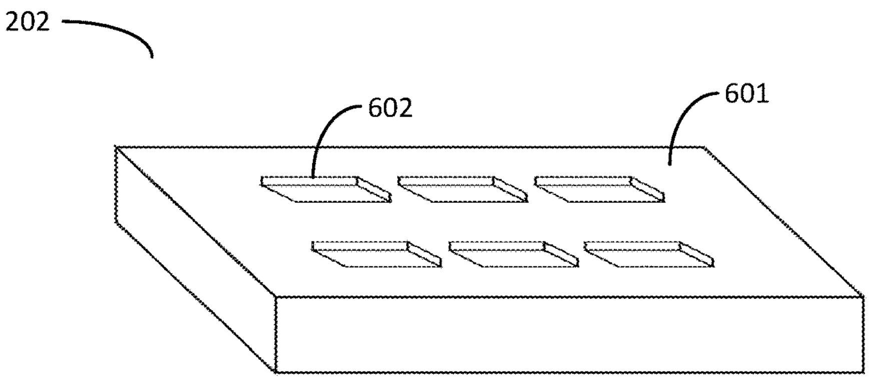
FIG. 6 depicts a perspective view of the charging device in accordance with an embodiment.
Figure 6A:
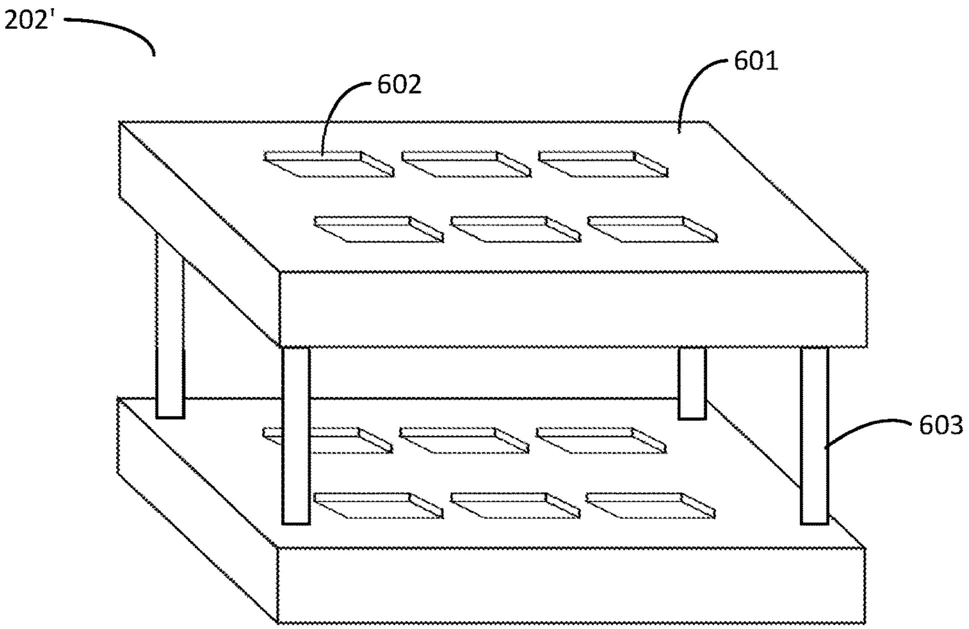
Figure 6B:
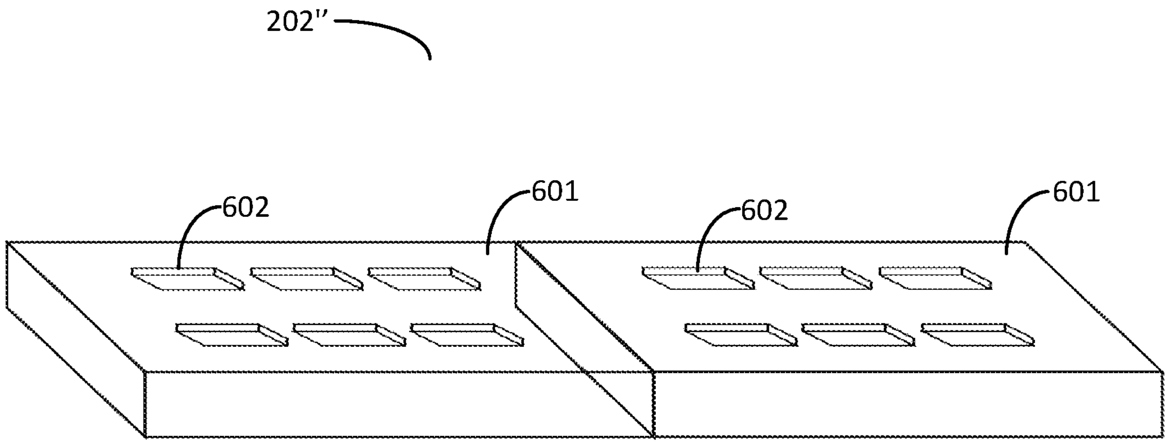
Figure 7:
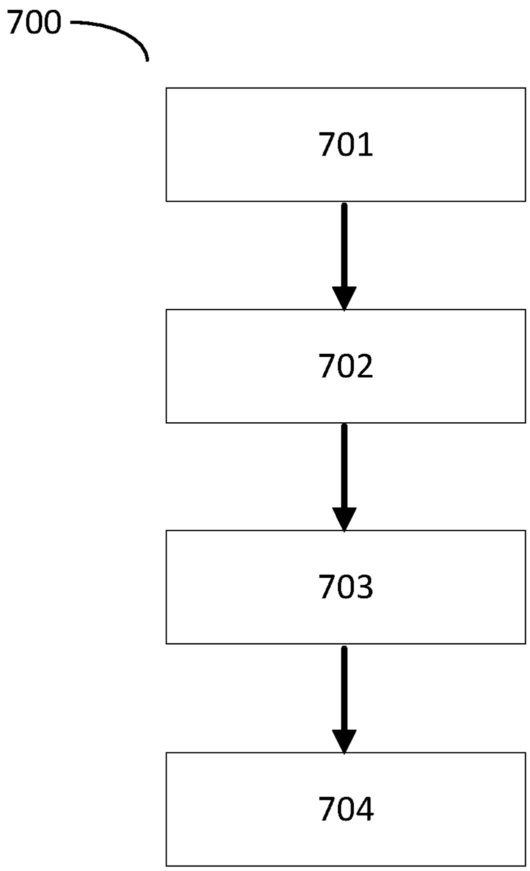
Figure 8:
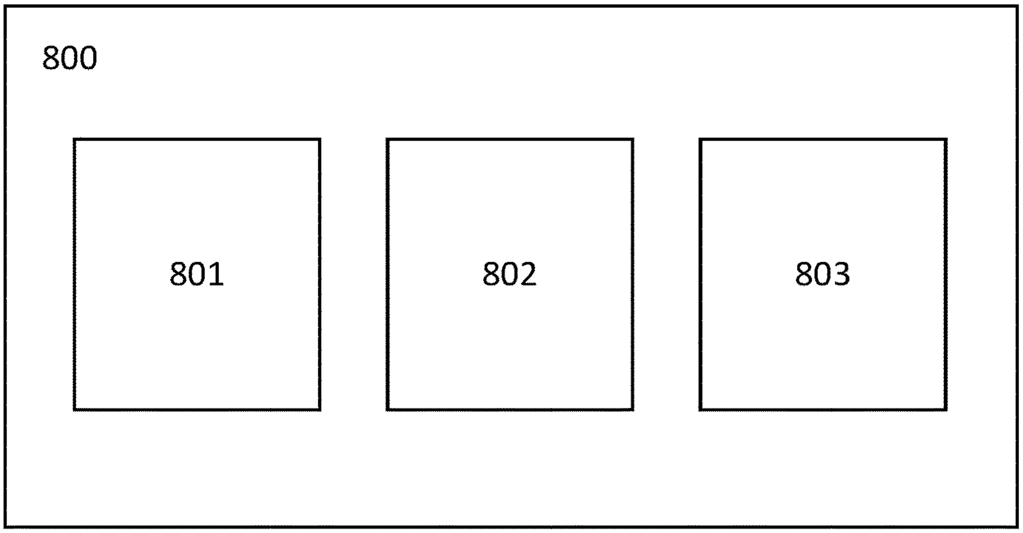
Figure 9:
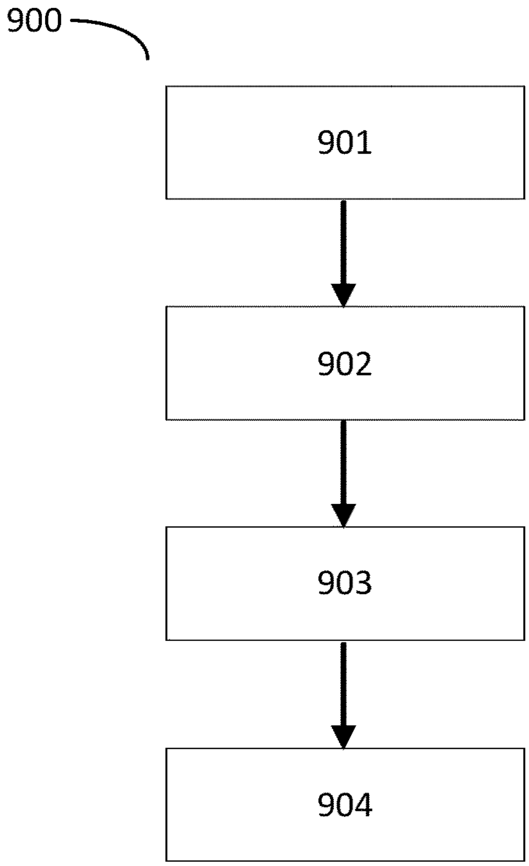
Figure 10A:
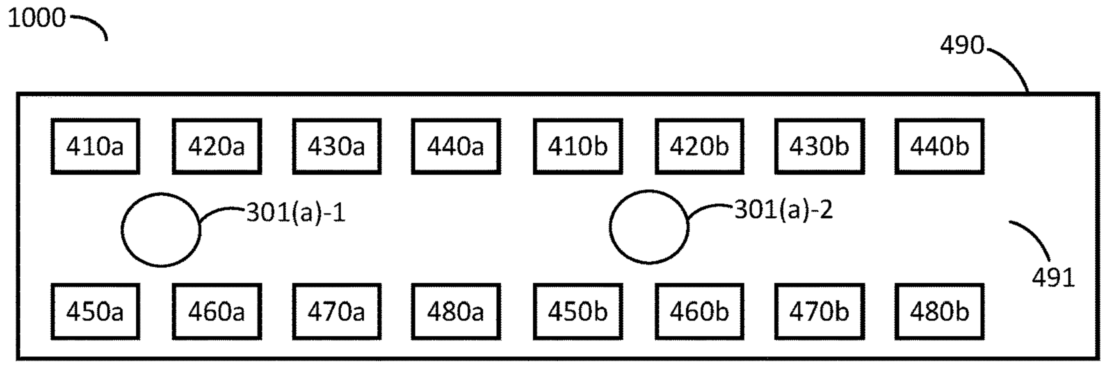
Figure 10B:
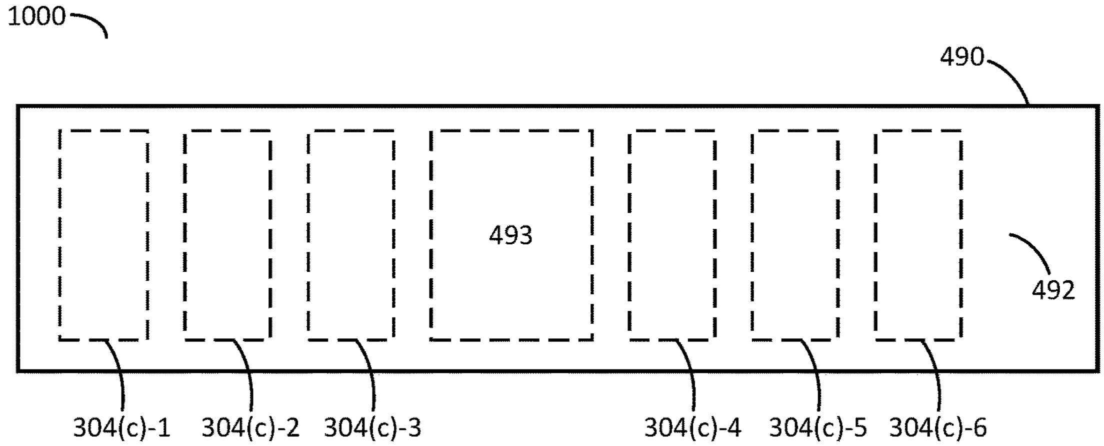
Figure 10C:
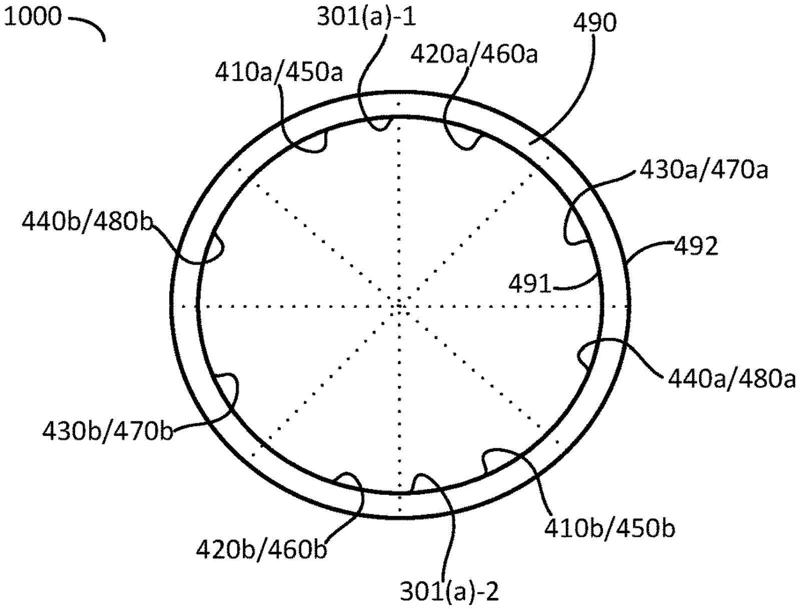
Figure 11:
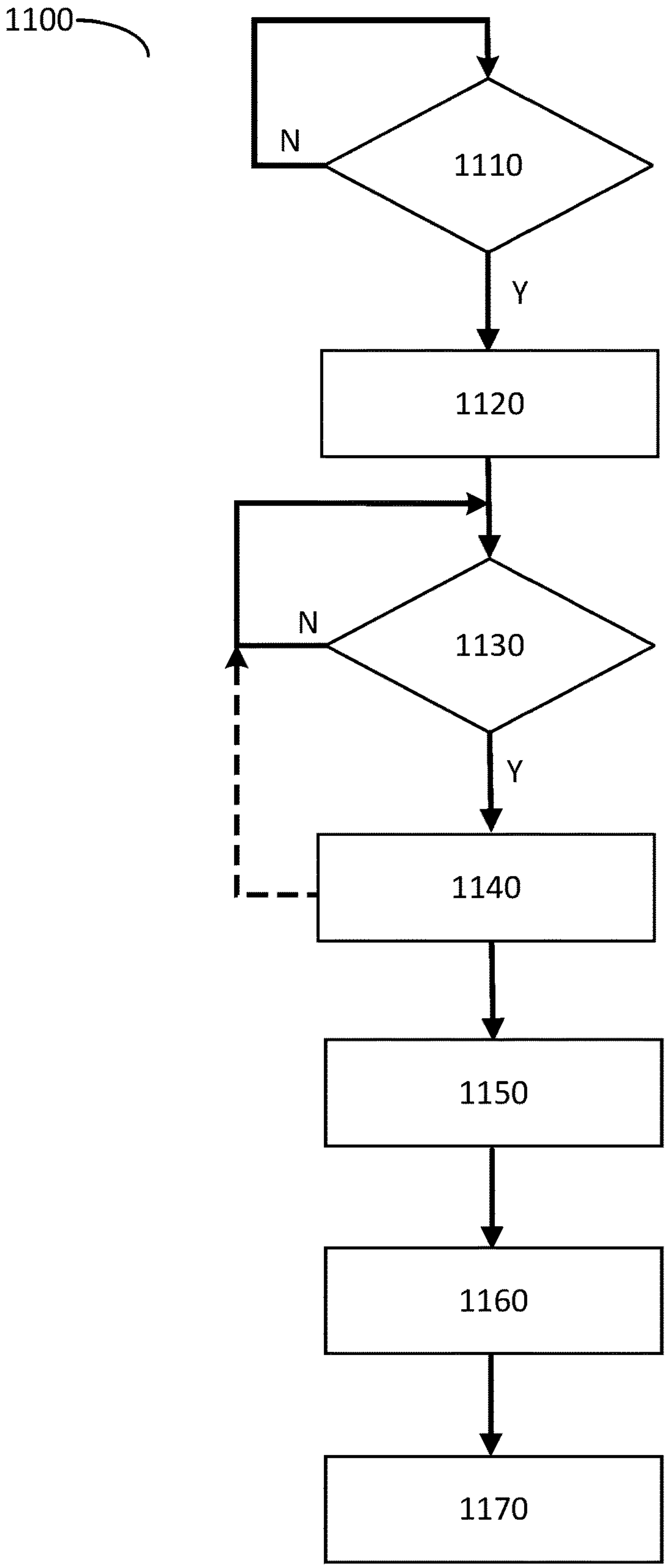

FIG. 6*a* depicts a perspective view of two charging devices arranged in a stacking manner in accordance with an embodiment;

FIG. 6*b* depicts a perspective view of two charging devices that are connected horizontally in accordance with an embodiment;

FIG. 7 depicts a flowchart of the self-starting algorithm employed by the sensing device to enable automatic data recording in accordance with an embodiment;

FIG. 8 depicts a block diagram of the online analysis platform in accordance with an embodiment; and FIG. 9 depicts a flowchart of deterministic analysis performed by the data analysis function block of the online analysis platform in accordance with an embodiment;

FIG. 10*a* depicts a plan view of the inner side of a detachable armband in an unfolded state, the armband comprising two pulse oximeters and one ECG sensor with multiple (e.g., eight) pairs of dry electrodes in accordance with an embodiment;

FIG. 10*b* depicts a plan view of the outer side of the detachable armband (e.g., as shown in FIG. 10*a*) in an unfolded state in accordance with an embodiment;

FIG. 10*c* depicts a side view of the detachable armband (e.g., as shown in FIG. 10*a*) in a folded state in accordance with an embodiment; and FIG. 11 depicts a flowchart of a different algorithm employed by the sensing device comprising a pulse oximeter and an ECG sensor in accordance with an embodiment.

Figure 1:
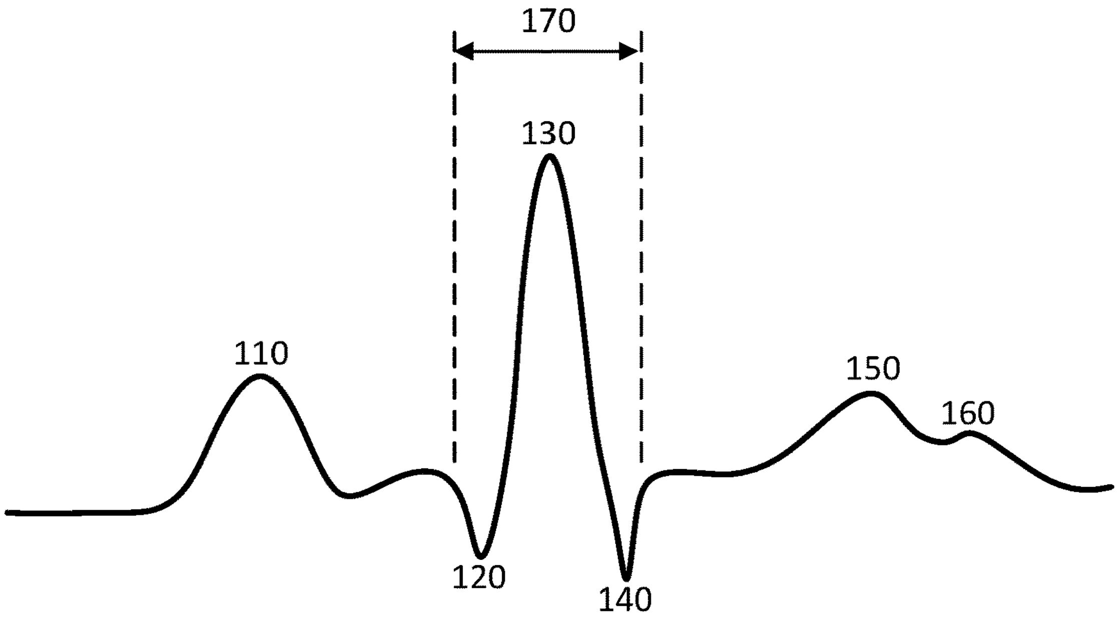
FIG. 1 depicts features of an example heart rhythm waveform.

With reference to FIG. 1, there is illustrated an example electrocardiogram of a single heartbeat. The electrocardiogram is a tracing of the electrical activity taking place within a heart. Under normal circumstances, an electrical impulse travels from the sinoatrial node, across the atrium and to the atrioventricular node and through the ventricular septum of the heart. Excited by the electrical impulse, the four chambers of the heart contract and relax in a coordinated manner. As illustrated in FIG. 1, the example electrocardiogram of a single heartbeat comprises multiple peaks and troughs representing different stages of heart beating. The peaks and troughs are denoted from the left to right as P-wave 110, Q-wave 120, R-wave 130, S-wave 140, T-wave 150 and U-wave 160, among which the P-wave 110 and the R-wave 130 are the most important features for detecting heart arrhythmia.

The P-wave 110 represents the atrial contraction and indicates the atrial depolarization. The Q-wave 120, R-wave 130 and S-wave 140 are named as QRS complex 170 which represents the electrical impulse as it spreads through the ventricles and indicates ventricular depolarization. The QRS complex 170 starts just before ventricular contraction. The T-wave 150 following the QRS complex 170 indicates ventricular repolarization. Heartbeat regularity is established by measuring time intervals between any two successive R-wave 130 peaks. Fibrillation of the atria is indicated by the absence of the P-wave 110. Measurement of irregular contractions of the atria and monitoring heart rate relative to the activity level of a patient are both important for identification of AFib. Note that not all pulsatile features indicative of some smaller waveform features displayed in FIG. 1 are easily measurable using pulse oximetry. For example, pulsatile characteristics representing the action driving the P-wave 110, Q-wave 120, S-wave 140, T-wave 150, and U-wave 160 present detection challenges due to either being caused by actions within the heart which occur before the opening of the tricuspid valve, or not resulting in large heart contractions which are detectable via haemoglobin level differences in the bloodstream Typically, a silent AFib patient will not physically feel any symptoms, and will not know they are at a significant risk of stroke. Hence, identification of AFib relies on a system which can be used over a prolonged period of time during everyday activities. As conventional wearable ECG is not suitable for everyday, continuous use, the invention seeks to provide everyday and a prolonged monitoring approach which can accurately and reliably capture critical AFib-indicative features, e.g., P-waves and R-waves. As mentioned above, the sampling frequency of existing pulse oximetry based devices typically lies in the range of 5 Hz and 215 Hz. A low sampling rate (and thus low temporal resolution) will only allow pulse oximeters to measure a parameter called the 'first derivative photoplethysmogram', which gathers information on blood oxygenation levels by measuring blood flow through large vessels. By contrast, detecting volume changes in small vessels (capillaries) using a high sampling rate (and thus high temporal resolution) will allow pulse oximeters to measure a parameter called the 'second derivative photoplethysmogram' (SDPPG), which can provide insights into the functionality of the heart chambers. In order to meet the demand of high temporal resolution required for high fidelity heart rhythm waveform or for accurate ECG-triggering, a pulse oximetry based monitoring device that is capable of providing a sampling rate of over 215 Hz, and preferably over 500 Hz, is highly desired.

Figure 2:
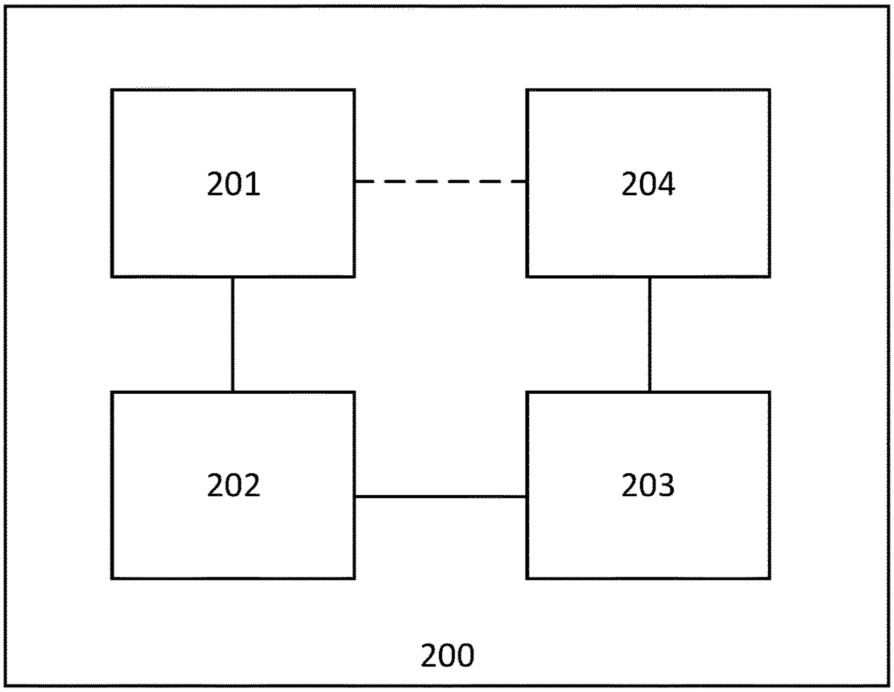
FIG. 2 depicts a block diagram of a system for detecting heart rhythm abnormalities in accordance with an embodiment.

With reference to FIG. 2, there is illustrated a block diagram of the heart arrhythmia detecting system 200 in accordance with an embodiment. The block diagram shows the core components of the system and the relationship between them. In some embodiments, the system may comprise a wearable heart rhythm monitoring device (or sensing device) 201, a charging device 202, a computing device 203, and an online analysis platform 204. In some embodiments, the charging device 202 may incorporate all the functions of the computing device 203 and thus a separate computing device will not be needed. In other embodiments, the heart arrhythmia detecting system 200 may comprise one or more other functional components that are not illustrated in the block diagram of FIG. 2. The sensing device 201 may be configured to collect data from the bloodstream of a person, e.g., a patient, which can be used later to derive a high fidelity heart rhythm waveform. The charging device 202 in connection with the computing device 203 may be configured to charge the sensing device 201 and enable data transfer from the sensing device 201 to the computing device 203. The computing device 203 in connection with the internet, may be configured to receive the data from the sensing device 201, and subsequently or simultaneously upload the data to the online analysis platform 204. In some embodiments, the online analysis platform 204 may be run on a remote server and may be configured to further process the data, analyse the processed data and finally generate an evaluation report.

Figure 3:
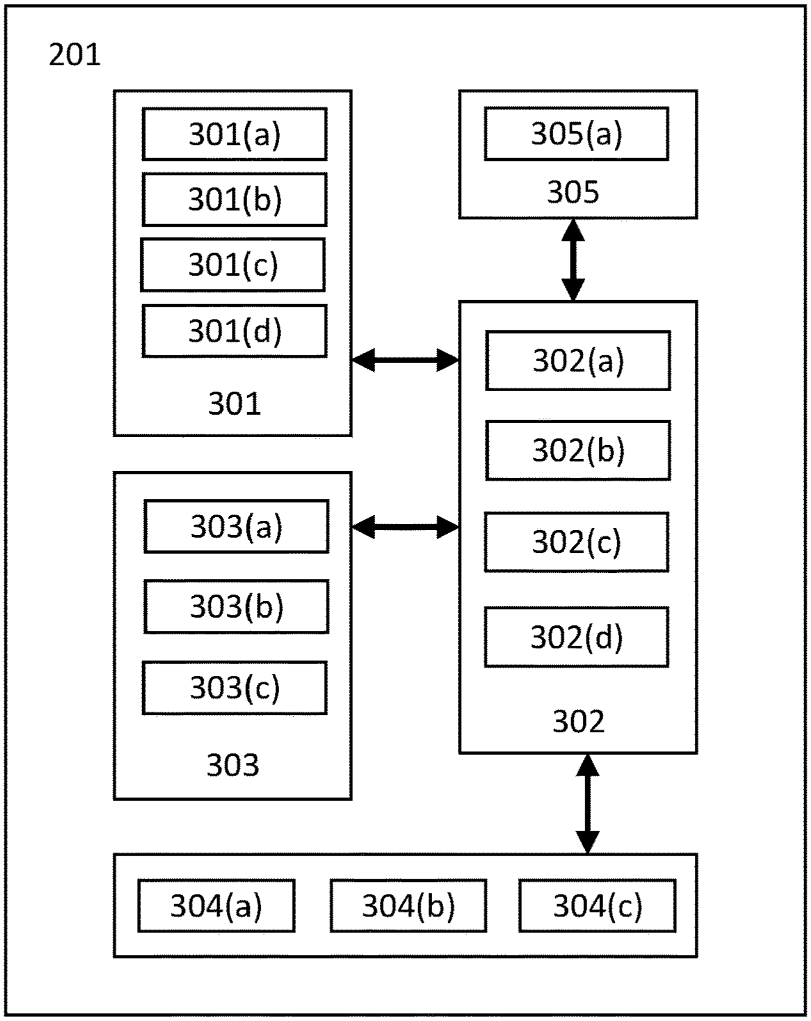
FIG. 3 depicts a block diagram of the sensing device used in the system for detecting heart rhythm abnormalities in accordance with an embodiment.

Each of above-mentioned core components will be described in detail below. With reference to FIG. 3, there is illustrated a block diagram of the functional components of the sensing device 201 and their interactions in accordance with an embodiment. In the embodiment, the sensing device 201 comprises a sensor unit 301, a processor unit 302, a memory unit 303, a power unit 304, and an interface unit 305.

In some embodiments, the sensor unit 301 may comprise at least one multi-channel pulse oximeter 301(*a*), at least one tri-axis accelerometer 301(*b*) and at least one internal temperature sensor 301(*c*). The multi-channel pulse oximeter 301(*a*) may comprise a light emitter emitting at least two optical wavelengths. In some embodiments, the multi-channel pulse oximeter 301(*a*) may emit wavelengths in blue, green, yellow, red, and infrared wavelengths between 400 and 970 nm, cycling between them periodically dependent on activity levels, and as charge levels vary. In other embodiments, the multi-channel pulse oximeter 301(*a*) may only emit two wavelengths, i.e. 660 nm and 940 nm, sequentially and periodically. The sampling frequency of the multi-channel pulse oximeter may be controlled by the processor unit 302. The multi-channel pulse oximeter 301(*a*) may be operable at a high sampling rate. In some embodiments, the sampling rate may be preferable to be greater than 215 Hz. In other embodiments, the sampling rate may be preferable to be greater than 500 Hz. In different embodiments, the sampling rate may be adjustable for example, between 5 Hz and 1000 Hz, between 215 Hz and 500, between 215 Hz and 800 Hz, or between 215 Hz and 1000 Hz.

In some embodiments, the sensor unit 301 may further comprise a tri-axis accelerometer 301(*b*). The tri-axis accelerometer may be used to track motion of a wearer. Every time the pulse oximeter 301(*a*) is sampled, so is the accelerometer 301(*b*) such that there are corresponding data points for every logged sample. The pulse oximeter 301(*a*) picks up signals caused by motion, and signals derived from blood volume changes within vessels. The accelerometer 301(*b*) picks up signals caused by motion alone. Subtracting one from the other leaves signals due to blood volume changes. Within the device, signals from both the pulse oximeter 301(*a*) and, accelerometer 301(*b*) are committed to memory, with processing done later via algorithms hosted on the online analysis platform 204.

In some embodiments, the sensor unit 301 may further comprise an internal temperature sensor 301(*c*). The internal temperature sensor 301(*c*) ensures that the sensing device 301 is running at a safe temperature. In addition to its standard use as a safety feature (whereby devices are powered down should they exceed a certain temperature threshold), the temperature data may be used to further refine system architecture over time by analysing trends in device temperature changes over time. Temperature data may be logged at regular intervals to infer additional information about patient activity.

In some embodiments, the sensor unit 301 may further comprise one or more circuits for noise reduction and/or signal amplification. The noise reduction circuit may comprise a low pass filter configured to remove motion induced low frequency noise on the sensor signal. The signal amplification circuit may allow the sensor signal to be amplified to a certain level required by the processor unit 302.

In some embodiments, the sensor unit 301 may further comprise an ECG sensor 301(*d*). The ECG sensor 301(*d*) may comprise an ECG circuit and one or more pairs of electrodes electrically connected to the ECG circuit. The ECG sensor 301(*d*) may be configured to measure an electrical potential difference or electrical voltage between each pair of electrodes which are attached to two locations of the body surface. The electrodes may preferably be dry electrodes that can be attached directly to the body surface without requiring use of electrolytic gel. Each electrode may be in the form of a conductive pad or strip. In some embodiments, multiple pairs of dry electrodes may be preferable over a single pair because more electrodes help improve the chances that one will record a good quality (e.g., high signal to noise ratio) ECG signal. In such cases, the ECG sensor 301(*d*) may be configured to generate multiple electrical voltage signals at any given point of time, each being obtained by measuring the electrical voltage between one pair of dry electrodes. Additionally or optionally, the ECG sensor 301(*d*) may be configured to associate each time-dependent electrical voltage signal to a corresponding pair of dry electrodes through which the electrical voltage signal is generated. Additionally or optionally, the ECG sensor 301(*d*) may be configured to perform real-time processing of the multiple electrical voltage signals. The real-time processing may comprise for example amplifying the originally weak electrical voltage signals and subsequently filtering the amplified electrical voltage signals. Note that, part or all of such real-time data processing may be performed by other on-board circuits, such as the aforementioned one or more circuits for noise reduction and/or signal amplification.

In some embodiments, the ECG sensor 301(*d*) may be configured such that it can be switched between two operating modes, i.e. an idling mode and an active mode. When in the idling mode, the ECG sensor 301(*d*) may not measure electrical voltages (and thus generate electrical voltage signals) from multiple pairs of electrodes. However, when in the active mode, the ECG sensor 301(*d*) may continuously measure the electrical voltage between each pair of electrodes at a given sampling rate, such as the sampling rate set for the multi-channel pulse oximeter 301(*a*), as described above.

In some embodiments, the processor unit 302 may further comprise an arithmetic logic unit 302(*a*), a control unit 302(*b*), register arrays 302(*c*) and firmware 302(*d*). The arithmetic logic unit 302(*a*) performs arithmetic and logic operations guided by the control unit 302(*b*) on data from the input registers. The corresponding result is stored on an output register. The control unit 302(*b*) directs the operations of the process unit 302. It controls the logic behind arithmetic logic unit 302(*a*), the register arrays 302(*c*) and input and output devices on how to respond to the firmware instructions. Registers 302(*c*) are small amounts of storage within the processor unit 302. Input registers store data from the external sensors, e.g., sensors in the sensor unit 301, the control unit 302(*b*) guides the arithmetic logic unit 302(*a*) on what operations to perform on the data based on the firmware instructions and the corresponding results from the arithmetic logic unit 302(*a*) are stored in output registers for transfer back to the external sensors. The system firmware 302(*d*) controls the functionality of each of e.g., the inputs, storage, and power management on-board the device.

In some embodiments, the sensing device 201 may comprise at least two processor units, e.g., a primary microcontroller unit MCU and a secondary MCU. The two MCU units may be configured to work in a complementary manner.

In some cases, the primary MCU may be configured to continuously process and analyse samples from the pulse oximeter 301(*a*) and accelerometer sensor 301(*b*) which are then written to memory. The primary MCU may be configured to dynamically change the polling rate of these sensors based on off-nominal changes in readings i.e. those caused by motion artefacts. This ability assists in recording high quality heart waveforms, and obtaining accurate beat-to-beat timings so that on-board components or modules (e.g., cellular module 305(*a*), ECG sensor 301(*d*)) can be activated at an appropriate time. The primary MCU may be configured to dynamically alternate between sleep and active mode between sample collections. This greatly reduces energy consumption due to the low power requirements of the primary MCU while in an inactive state. Due to a multitude of superfluous features, the processors of comparable devices are required to process multiple tasks simultaneously, meaning the processor needs to be in active mode continuously, greatly reducing the overall runtime capabilities. Based on sensor readings, the primary MCU can trigger the secondary MCU to execute certain actions, such as for example, entering sleep-mode when the device is not being worn.

The secondary MCU may be configured to process and analyse multiple sensor inputs (e.g., inputs from the pulse oximeter 301(*a*) and/or ECG sensor 301(*d*)), and conduct actions in response. The secondary MCU may remain in a low power sleep state until it is woken at predefined time intervals (to check if the device is being worn), or when triggered by the primary MCU. The primary MCU may be configured to execute 'interrupts' on the secondary MCU (e.g., instructing it to perform a different task based on sensor inputs). When the secondary MCU is woken from the sleep state after predefined time periods, it may for example take battery level readings, circuit performance readings, and ambient temperature readings, all of which are written to the devices memory. This data will be used internally to better understand how the device performs in various environments.

In some embodiments, the memory unit 303 may further comprise a real-time clock 303(*a*), a random access memory 303(*b*) and an on-board memory 303(*c*). The real-time clock 303(*a*) keeps track of the time. The processor unit 302 may read this time and append a timestamp to every data log committed to the device's internal memory. The real-time clock 303(*a*) may be refreshed every time the sensing device 201 is returned to a charging station in order to compensate for time-slips (RTC's are highly accurate, but not perfect and need to be refreshed periodically). The random access memory 303(*b*) may be used to temporally store the sampled data before it being arranged appropriately, encrypted by the processor unit 302, and eventually committed to long-term on-board memory 303(*c*). The on-board memory 303(*c*) may be in the form of flash storage designed to hold the gathered, encrypted data. This memory 303(*c*) may be wiped after successful confirmation of data uploading to the online portal. The write-rate of the on-board memory may be tailored to match the unusually high throughput demands caused by multiple streams of high-fidelity data.

In some embodiments, the power unit 304 may further comprise a power management integrated circuit 304(*a*), a battery charger 304(*b*), and a battery 304(*c*). The power management integrated circuit 304(*a*) disseminates power amongst the various electronic components. The processor unit 302, receiving information from the sensor unit 301, can influence the functionality of the power management integrated circuit 304(*a*) as the sampling rates are controlled by applying varying power levels to the sensors of the sensor unit 301, which in turn impacts battery longevity. The battery charger may be capable of receiving power from the charging device 202 and enabling fast-charging of the device's battery 304(*c*). The battery 304(*c*) itself may possess a large charge capacity in order to satisfy the need of long term continuous heart rhythm monitoring. The large charge capacity (hence a large battery size) is enabled by the large internal volume of the sensing device 201 after many superfluous features that are typically adopted in existing wearable heart rate monitors are removed. In some embodiments, the battery 304(*c*) may have a charge capacity in the range between 1000 milliamp-hour (mAh) and 3000 mAh. In other embodiments, the charge capacity may be in the range between 1200 mAh to 2200 mAh.

In some embodiments, the power unit 304 may further comprise a low dropout regulator which may act to maintain a constant voltage to the processor unit 302 and the sensor unit 301 regardless of the level of charge of the battery (for example, at full charge, the battery may be running at 4.2 V, and when near fully discharged the battery may be running at 2.7 V. The low dropout regulator maintains a constant 2.5 V regardless of this); a DC-DC converter may work in parallel to the low dropout regulator to convert a source of one DC voltage level to another level; and a smart reset which may only allow current to flow once the voltage reaches e.g., 2.5 V from the battery. When this has been reached, the PMIC is reset and the low dropout regulator maintains a constant 2.5V.

In some embodiments, the interface unit 305 may comprise components or modules (not shown in FIG. 3) that enable connections between the sensing device 201 and the outside world for the purposes of e.g., human interaction, data transfer and power charging. In some embodiments, the interface unit 305 may comprise a cellular module 305(*a*) (e.g., a 3G module or a 4G/LTE module) configured to allow data exchange (e.g., uploading data) between the sensing device 201 and a remote server via an existing mobile network. In some embodiments, the remote server may be the same server on which the online analysis platform 204 is run. In some embodiments, the cellular module 305(*a*) may only be activated in a short period of time sufficient to allow at least part of the recorded data (e.g., ECG data) comprising one or more flagged anomalous events to be transmitted to the remote server. Selectively transmitting data that is indicative of heart rhythm anomalies in the middle of a long (e.g., 90 days) and continuous recording session allows such data to be seamlessly and hastily sent to the server and then e.g., a medical doctor should an anomaly meriting near-immediate intervention occur at any time.

Figure 4:
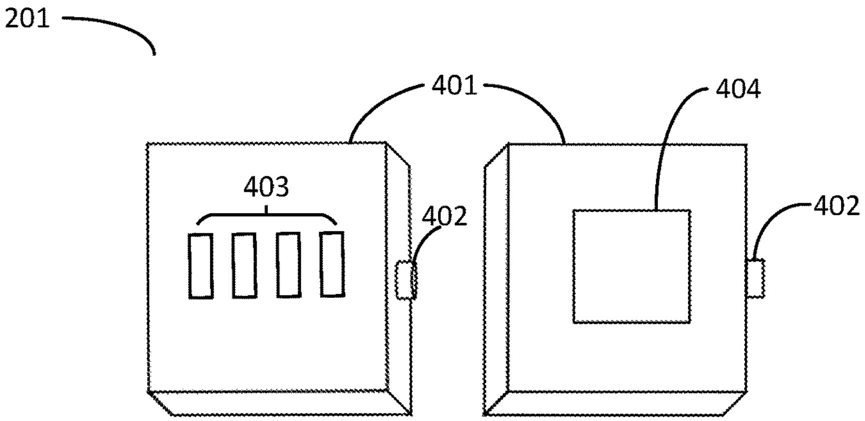
FIG. 4 depicts a perspective view of the sensing device in accordance with an embodiment.

FIG. 4 shows a perspective view of the sensing device 201 according to an embodiment. As shown in FIG. 4, the sensing device 201 may comprise an external casing 401 which encloses all the electrical components of sensing device 201 and is in direct contact with the wearer's body. When placed on the wrist, the external casing 401 may comprise fixing features allowing the external casing 401 to be connected to a wrist band or strap. In other embodiments, the sensing device 201 may be placed on the arm and may be facilitated by connecting the external casing 401 to an arm band or strap. Note that, the sensing device 201 may also be used on other different parts of the body. The wristband configuration may be preferable for some embodiments wherein the sensing device 201 comprises no ECG sensor 301(*d*) but only the pulse oximeter 301(*a*). Requiring no electrodes means a narrow band or strap (e.g., a wristband) having a relatively small contact area with the body skin can be used. The armband configuration may be desirable for other embodiments wherein the sensing device 201 comprises both the pulse oximeter 301(*a*) and the ECG sensor 301(*d*). In such cases, a wide band or strap (e.g., an armband) may be needed to accommodate one or more pairs of dry electrodes. The one or more pairs of dry electrodes may for example line the interior of the armband which will be positioned on the upper left arm. FIGS. 10*a* to 10*c* schematically depict an armband in accordance with an embodiment, which will be described below.

In some embodiments, the external casing 401 may comprise a button 402, multiple indication light emitting diodes (LEDs) 403 and an optical window 404. In some embodiments, the interface unit 305 may be configured to connect the processor unit 302 to the button 402 and indication LEDs 403. In some embodiments, the button 402 may be a mechanical and capacitive button and may be located on the peripheral area of the external casing 401 of the sensing device 201. Clicking the button 402 may add a timestamp to the data being recorded at that time, which may draw extra attention to that area when the data is reviewed. Touching the button 402 may cause the battery levels to display via indication LEDs 403 on the front face of the external casing for a short period of time. In some embodiments, the indication LEDs 403 may comprise for example four RGB LEDs. Each LED may represent 25% of battery remaining. All LED's displaying a constant yellow may mean the device is in 'programming mode' (for firmware updates). All LED's displaying a constant blue may mean the device is in 'docked mode'. All LED's flashing blue may mean the device is transferring data. All LED's flashing orange may mean the device is in 'detection mode' (e.g., the device is being paired with a newly created patient directory). In some embodiments, the optical window 404 may be located directly underneath the pulse oximeter 301(*a*) and may be transparent to all the wavelengths of the pulse oximeter 301(*a*).

In some embodiments, particularly those without any ECG sensor 301(*d*), part or all of the external casing 401 may be made of a polyurethane gel elastomer with a low refractive index. In different embodiments, only the bottom part of the external casing 401 which is in direct contact with the skin may be made of a polyurethane gel elastomer. This is expected to decrease motion induced interference caused by wearer activity via more effective impact absorption (or 'shake compensation') without compromising sensor readings that may be caused by the presence of an additional medium for the pulse oximeter light to travel through. Existing wearable devices use a fluoroelastomer to stabilise the sensor against the skin. The polyurethane gel elastomer possesses a higher friction coefficient than fluoroelastomers, providing enhanced stability through additional grip. In some embodiments, the external casing 401 may have a curved body shape designed to follow for example the wrist curvature. In this way, the stability of sensor connections can be further improved. In some embodiments, the sensing device 201 may adopt a contact point configuration where each contact of a data transfer and charging circuitry is internally rerouted to one metal contact point arranged on the external casing 401. The data transfer and charging circuitry may comprise for example a 4-pin USB circuitry.

FIG. 10*a* is a plan view of the inner side of a detachable armband 1000 in an unfolded state. As shown in the figure, the armband 1000 may comprise two pulse oximeters 301(*a*)-1, 301(*a*)-2 and one ECG sensor with eight pairs of dry electrodes 410*a*/410*b*, 420*a*/420*b*, 430*a*/430*b*, 440*a*/440*b*, 450*a*/450*b*, 460*a*/460*b*, 470*a*/470*b*, 480*a*/480*b*, all of which may be attached to the inner surface 491 of the armband 1000. The light-emitting side of the pulse oximeters 301(*a*) may be in direct contact with the body skin. Note that other embodiments may comprise different numbers of the sensing devices and dry electrodes other than those shown in the figure. The dry electrodes 410*a*/410*b*, 420*a*/420*b*, 430*a*/430*b*, 440*a*/440*b*, 450*a*/450*b*, 460*a*/460*b*, 470*a*/470*b*, 480*a*/480*b* may be for example flexible concentric ring electrodes although other different dry electrode designs that are commonly used for ECG are equally applicable.

FIG. 10*b* is a plan view of the outer side of the detachable armband 1000 in the unfolded state. The armband 1000 may comprise a plurality of batteries (e.g., six batteries 304(*c*)-1-304(*c*)-6 in this particular embodiment) and a main electrical circuit board (PCB) 493 comprising the ECG circuit of the ECG sensor. In the embodiment shown in FIGS. 10*a* and 10*b*, the main PCB 493, batteries 304(*c*)-1-304(*c*)-6, pulse oximeters 301(*a*)-1, 301(*b*) and dry electrodes 410*a*/410*b*, 420*a*/420*b*, 430*a*/430*b*, 440*a*/440*b*, 450*a*/450*b*, 460*a*/460*b*, 470*a*/470*b*, 480*a*/480*b* may form the sensing device 201. In different embodiments, the pulse oximeters 301(*a*) may be mounted on the PCB 493 from the inner side of the armband 1000. As shown in FIG. 10*b*, the plurality of batteries may be equally spaced along the length of the armband 1000. In some embodiments, the batteries 304(*c*)-1, 304(*c*)-2, 304(*c*)-3, 304(*c*)-4, 304(*c*)-5, 304(*c*)-6 may be embedded in the body of the armband 1000, the body of the armband 1000 being defined as the part between the inner surface 491 and the outer surface 492. Alternatively, in other embodiments, the plurality of batteries 494*a*-494*f* may be attached to the outer surface 492 of the armband 1000. The pulse oximeters 301(*a*) and all the dry electrodes 410*a*/410*b*, 420*a*/420*b*, 430*a*/430*b*, 440*a*/440*b*, 450*a*/450*b*, 460*a*/460*b*, 470*a*/470*b*, 480*a*/480*b* may be electrically connected with the main PCB 493 which may be embedded in the body of the armband 1000.

FIG. 10*c* is a side view of the detachable armband 1000 in a folded state. As shown in the figure, the dry electrodes 410*a*/410*b*, 420*a*/420*b*, 430*a*/430*b*, 440*a*/440*b*, 450*a*/450*b*, 460*a*/460*b*, 470*a*/470*b*, 480*a*/480*b* may be carefully positioned on the armband 1000 such that when the armband is folded to tightly grip the left arm bicep, the two electrodes of each electrode pair are on the opposite sides of the arm and facing each other. Note that the electrodes 410*a*/450*a*, 420*a*/460*a*, 430*a*/470*a*, 440*a*/480*a*, 410*b*/450*b*, 420*b*/460*b*, 430*b*/470*b*, and 440*b*/480*b* are all spatially separated along the direction normal to the plane of the figure. As shown in the figure, the electrodes 410*a*, 420*a*, 430*a*, 440*a*, 450*a*, 460*a*, 470*a*, 480*a* and the respective corresponding electrodes 410*b*, 420*b*, 430*b*, 440*b*, 450*b*, 460*b*, 470*b*, 480*b* are located on the opposite side of the arm (not shown) and facing each other. Such an arrangement may maximise the distance between each electrode pair and thus electrical potential difference measured through the pair.

Figure 5:
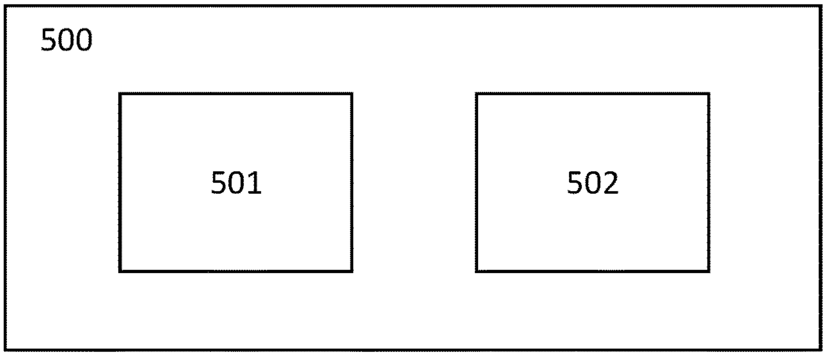
FIG. 5 depicts a block diagram of the charging device used in the system for detecting heart rhythm abnormalities in accordance with an embodiment.

With reference to FIG. 5, the charging device may possess data transfer and charging connection points complementary to the sensing device. The charging device 202 may comprise an AC-DC Converter 501 which converts the mains AC supply to DC power usable by the charging device 502, and a data transfer and charging circuitry unit 502 which is complementary to the contact points of the sensing device 201. The charging device 202 may be configured to comprise internally rerouted data transfer and charging connectors to receive and make contact with the metal contact points on the sensing device 201. When the two devices are in physical contact with each other, each of the metal contact points on the sensing device 201 connects to the corresponding metal contact point on the charging device 202 and thus a connection is established. A number of the metal contact points may be used for data transfer between the on-board memory 303(*c*) and the computing device 203. The other metal contact points may be used for charging. The complementary data transfer and charging connections between the sensing device 201 and the charging device 202 may be based on protocols such as for example USB 3.0, USB-C, or RS232.

With reference to FIG. 6, in some embodiments, the charging device 202 may comprise a plurality of charging bays, each being configured to accommodate a single sensing device. Each charging bay may correspond to a cavity recessed from the top surface of the body of the charging device 202. The dimensions of the recessed cavity may be slightly larger than those of the sensing device 201. The secure seating and connection may be achieved via the use of one or more magnets located in both the device body and charging bay. The contact points on each side allow for broad lateral expandability so that a mesh of charging bays can be created horizontally whilst minimising the number of necessary cables to two (e.g., one power cable and one USB cable). Depending on application, each charging device 202 may comprise 5, or 10, or 15, or 20, or 30 charging bays. With reference to FIG. 6(*a*), in some embodiments, two or more individual charging devices 202 may be stacked vertically to form a composite charging device 202' and can work in parallel by sharing the same electrical supply. Two charging devices 202 may be connected vertically using mechanical means, e.g., four posts 603. Alternatively, or additionally, two or more individual charging devices 202 may be connected horizontally to form a composite charging device 202" (as shown in FIG. 6(*b*)), thereby further increasing expandability of the charging device 202. Two charging devices 202 may be connected horizontally using mechanical means, e.g., two dowel joints (not shown), or magnetically.

In order to obtain high fidelity waveforms that are capable of revealing certain fine features in relation to heart rhythm abnormalities, such as for example the absence of the p-wave 110 or enable the accurate triggering of the on-board ECG, the multi-channel pulse oximeter 301(*a*) and accelerometer 301(*b*) may preferably have a sampling rate between 215 Hz and 1000 Hz. In some embodiments, the sampling rate may be dynamically adjusted in the range between 215 Hz and 1000 Hz by the processor unit 302 (as controlled by the system firmware 302(*d*)) in response to a predetermined event. The predetermined event may be for example an increased physical activity, a change in signal quality, or a decreased battery level. For example, data measured by the accelerometer 301(*b*) may be used to at least partially determine the sampling rate through detecting increased activity levels, which the processor unit 302 responds to by increasing the sampling rate of both the accelerometer and pulse oximeter. In such a manner, small features which are easily disguised by motion-induced interference can be recovered more readily by processing algorithms used later in the online analysis platform 204. Moreover, when quality of one or more sensor signals vary, the sampling rate may be also dynamically adjusted by the processor unit 302. For example, when the quality of the pulse oximeter signal degrades, the processor unit 302 may increase the sampling rate of both the accelerometer and pulse oximeter in order to substantially maintain a good data fidelity.

In parallel, a power-saving strategy may be employed which allows the sensing device 201 to decrease the rate of active sampling (e.g., from an initial rate of 1000 Hz to a later rate of 500 Hz) as battery-life decreases. The sampling rate may be reduced in a step-by-step manner and may be adjusted periodically. In some embodiments, the processor unit 302 may periodically check the remaining charge level of the battery 304(*c*) and calculate a percentage drop in the charge level over the last period of time. Then, the processor unit 302 may adjust/reduce the sampling rate by an amount proportional to the percentage change of the charge level of the battery 304(*c*). Fine control of the dynamic sampling rate contributes significantly to both the longevity of battery and the fidelity of the data. With the help of the dynamic sampling control and a large capacity battery, the sensing device 201 is able to provide a single continuous recording period of up to 90 days, or approximately 90 days, or greater than 90 days, thereby significantly increasing the detection rate of heart rhythm abnormalities, such as AFib.

In some embodiments, the processor unit 302, or more specifically the firmware 302(*d*), may be configured to maintain a virtually constant sampling rate when the sampling rate decreases as a result of the decrease of the battery charge or the increase of the wearer's physical activity. The virtually constant sampling rate may be maintained by applying interpolation to the data obtained with a decreasing sampling rate. Interpolation offers the ability to reduce the live sampling rate gradually over time, as battery life decreases, whilst preserving accuracy of the waveform. The extent to which interpolation is used will vary depending on battery performance. It may be used from the beginning to end of recording duration if necessary, as battery degradation occurs over time with repeat uses of the same device. For example, when the sampling rate has reduced from e.g., initial 1000 Hz to current 500 Hz as a result of discharging of the battery 304(*c*), the number of measured data points per second dropped correspondingly from 1000 to 500.

As mentioned above, insufficient sampling results in poor temporal resolution and therefore low fidelity heart rhythm waveform or inaccurate ECG-triggering. Hence, to compensate for such data point loss, interpolation density is increased accordingly such that the total number of data points (measured and interpolated) per second is maintained to be 1000, corresponding to a constant sampling rate of 1000 Hz. Interpolation may be performed on the measured data by the sensing device 201 while the data is being recorded. Alternatively, it may be performed on data post-collection in order to reduce signal noise attributable to physical motion and other environmental factors. This processing may be performed on the data analysis platform 204 and may be supplemental to the electrical filtering performed on-board the device. In some embodiments, different interpolation methods may be applied to different parts of the measured data. For example, in the case where the measured sensor signal changes linearly with time, linear interpolation will be applied. In the case where the measured sensor signal changes nonlinearly with time, polynomial interpolation will be selected. The application of interpolation allows the sensor unit (e.g., the multi-channel pulse oximeter in this case) to be operated at low sampling rates (e.g., between 5 Hz and 215 Hz) while simultaneously maintaining a sufficient number of data points and therefore ensuring a high fidelity heart rhythm waveform or accurate ECG triggering.

In some embodiments, the firmware 302(*d*) may format the data appropriately, perform encryption, and log the encrypted data to the on-board memory 303(*c*) live. In some embodiments, data formatting may comprise further software-based filtering and smoothing (e.g., Savitzky-Golay smoothing). Data encryption may be obtained by means of e.g., a cryptographic algorithm (algebraic matrix-based).

In some embodiments, the sensing device 201 may immediately begin detecting a heartbeat signal when placed on a part of a wearer's body. As soon as the heartbeat signal is detected and simultaneously meets one or more predefined conditions, the sensing device 201 may automatically begin recording of the data which may had been filtered, formatted and encrypted by the hardware as well as firmware of the sensing device 201. The firmware 302(*d*) may incorporate a self-starting algorithm for determining whether the sensing device can automatically start data recording. With reference to FIG. 7, the self-starting algorithm 700 may perform, for example, the following four steps.

At step 701, when not being worn, the sensing device 201 may be operated in an idle mode in which the processor unit 302 may command the sensor unit 201 to sample the bloodstream of the wearer once every e.g., 20 seconds for a duration of e.g., 3 seconds. If a heartbeat signal having an amplitude greater than a predefined threshold and features matching a predefined heart waveform is detected, the algorithm may proceed to step 702. Otherwise, the algorithm may stay at step 701.

At step 702, the processor unit 302 may check if the detected heartbeat signal having an amplitude greater than the predefined threshold and features matching the predefined heart waveform. Wearer heart rate may be compensated for by expanding and contracting the predefined heart waveform until a match with the measured heart activity is established. This may prevent noise from triggering automatic recording. If the heartbeat signal successfully matches the predefined criteria, the algorithm may then proceed to step 703. Otherwise, the algorithm may return to step 701.

At step 703, the processor unit 302 may further check if the heartbeat signal acquired during the 3-second sampling window matches substantially to a predefined heartbeat signal stored in the on-board memory 303(*c*), the algorithm may proceed to step 704. Otherwise, the algorithm may return to step 701.

At step 704, the processor unit 302 may allow the densely sampled raw data to be processed and encrypted before being committed to the on-board memory 303(*c*). Data recording will continue unless the amplitude of the heartbeat signal drops below the predefined threshold, in which case, the algorithm will repeat steps 701 to 703 until a new recording session is established.

In some embodiments, the firmware 302(*d*) may incorporate a different algorithm for the cases where the pulse oximeters 301(*a*) and the ECG sensor 301(*d*) are both present in the sensing device 201 and are used together, e.g., the armband 1000 shown in FIGS. 10*a*-10*c*. The algorithm, when executed by the processor unit 302, may perform both self-starting and auto-reporting functions. The self-starting function may allow the sensing device 201 to determine whether the sensing device 201 can automatically start data recording; while the self-reporting function may allow the sensing device 201 to transfer data captured during anomalous events. It may allow the captured data to be transferred immediately after the event, or as a batch on a daily basis. With reference to FIG. 10 and FIG. 11, the algorithm 1100 may perform for example the following seven steps.

At step 1110, the processor unit 302 may determine whether the armband 1000 is being worn. Both the pulse oximeters 301(*a*)-1, 301(*a*)-2 and the ECG sensor 301(*d*) may be activated. The processor unit 302 may command the ECG sensor to periodically measure voltage differential across each electrode pair 410*a*/410*b*, 420*a*/420*b*, 430*a*/430*b*, 440*a*/440*b*, 450*a*/450*b*, 460*a*/460*b*, 470*a*/470*b*, 480*a*/480*b* and compare the measured voltage differential to a threshold level. In cases where one or more electrical voltage signals received from the ECG sensor 301(*d*) are higher than the threshold level, the processor unit 302 may determine that the armband 1000 is being worn and may move to step 1120. Otherwise, the processor unit 302 may stay at step 1110.

At step 1120, once the processor unit 302 determines the armband 1000 is being worn, the processor unit may initiate a full data recording session which may last for example 90 days. At this stage, only the pulse oximeters 301(*a*)-1, 301(*a*)-2 is activated while the ECG sensor is set to the idling mode. The processor unit 302 may monitor peak-to-peak (P-P) pulse timings live and compute their regularity by comparing the P-P interval of the last detected beat with previous beats (e.g., the previous 5-10 beats).

At step 1130, the processor unit 302 may determine whether there is any irregularity exist in the P-P pulse timings. This may be achieved for example by checking if the standard deviation of the P-P intervals rises over time. A rising standard deviation indicates either irregularity, or exercise-induced increase in heart rate. The latter can be ruled out via accelerometer measurements, for example. The processor unit 302 may determine the existence of irregularity for example by comparing the standard deviation to an ECG triggering threshold. If the standard deviation of the P-P intervals is lower than the ECG triggering threshold, the processor unit 302 may stay at step 1130 and continue to monitor the P-P pulse timings. If the standard deviation of the P-P intervals is equal to or higher than the ECG triggering threshold, the processor unit 302 may proceed to step 1140.

At step 1140, the processor unit may activate the ECG sensor 301(*d*) and initiate ECG recording. While the ECG data is being recorded, the pulse data generated by the pulse oximeters 301(*a*)-1, 301(*a*)-2 is also being recorded and analysed in an unaffected manner. In some embodiments, the ECG data may be stored in the same on-board memory 303(*c*) where the pulse data measured by the pulse oximeters 301(*a*)-1, 301(*a*)-2 is stored. In different embodiments, the ECG data may be stored in a different on-board memory 303(*c*). The parallel operation of the pulse oximeters 301(*a*)-1, 301(*a*)-2 and the ECG sensor 301(*d*) may allow the ECG sensor to be activated only when pulse irregularity is determined, thereby reducing the energy consumption of the sensing device 201. In some embodiments, the ECG sensor may be deactivated by the processor unit 302 after a fixed duration of time, which may be, for example, a fixed duration of 20 minutes, a fixed duration of 30 minutes, or a fixed duration of 40 minutes. Alternatively, in other embodiments, the ECG sensor may be deactivated if no irregularity in the P-P pulse timings had been identified in a most recent duration of time, which may be, e.g., a most recent 5 minutes, or a most recent 10 minutes. Once the ECG sensor 301(*d*) is deactivated, the processor unit 302 may stop the ECG data recording and move to step 1150. Each individual ECG recording session may result in one or more ECG traces, each comprising associated with one electrode pair.

At step 1150, the processor unit 302 may analyse the quality (e.g., signal to noise ratio) of each ECG trace and select the ECG trace with the best signal to noise ratio. The processor unit 302 may then progress to step 1160.

At step 1160, the processor unit 302 may activate the cellular module 305(*a*) so as to establish a connection between the remote server and the sensing device 201. Once the connection is established, the processor unit 302 may initiate transmission of the selected ECG data to the remote server via the cellular module 305(*a*). Along with the ECG data, other information associated with the sensing device 201, such as for example, the remaining space in the memory unit, a diagnostic log of all the device components, and present battery level, may also be transmitted to the remote server. If the cellular module 305(*a*) cannot establish a connection with a remote server, an interrupt may be sent to the processor unit 302 to deactivate the cellular module 305(*a*) and maintain the current data in the on-board memory 303(*c*). Following a failed connection attempt, a number of additional attempts may be made periodically. Failing these, the processor unit 302 may continue to make attempts on a daily basis, for example, on the next daily scheduled secondary MCU transmission wake up. Upon completing the data transmission, the processor unit 302 may progress to step 1170.

At step 1170, the processor unit 302 may check if the cellular module 305(*a*) receives a signal from the remote server confirming the successful transmission of all data and may subsequently deactivate the cellular module 305(*a*). In some embodiments, the processor unit 302 may clear all the recorded ECG data in the on-board memory 303(*c*) so as to prepare for the next session of ECG recording.

After successfully receiving the ECG data, the remote server may perform deterministic analysis on the ECG trace to determine e.g., presence of AFib. The deterministic analysis may be performed by an application run on the remote server, such as for example, the online analysis platform 204. The deterministic analysis is described in detail below with reference to FIG. 9.

With reference to FIG. 2, in some embodiments, the computing device 203 may be a general purpose computer that is connected to the internet via an Ethernet cable. The computing device 203 may be connected to the charging device 202 via a USB cable to allow data transfer from the sensing device 201. In some embodiments, a dedicated software application may be installed on the computing device 203 which enables the communication between the computing device 203 and the online analysis platform 204. In other embodiments, the online analysis platform may be accessed by a web browser installed on the computer device 203. In some embodiments, the data received from the sensing device 201 may be temporally stored in a folder created for containing the data from this particular device. In other embodiments, the data stored in the sensing device 201 may be directly uploaded to the online analysis platform via the dedicated software application or the web browser without being stored in the computing device. In this way, privacy protection of the system may be enhanced.

With continued reference to FIG. 2, the online analysis platform 204 may be a cloud based data hub which allows for development and implementation of various cloud-based algorithms. In some embodiments, the online analysis platform 204 may further comprise a data processing function block 801, a data analysis function block 802 and a database 803. The data processing function block 801 may comprise one or more data processing algorithms employed to decrypt the data, further process the data and generate a high fidelity heart rhythm waveform. The data analysis function block 802 may comprise one or more data analysis algorithms configured to perform deterministic analysis on the heart rhythm waveform and identify features that are capable of indicating any heart rhythm abnormalities. The data analysis function block 802 may also generate an analysis report based on findings of the analysis. The database 803 may be used to contain the high fidelity heart rhythm waveforms and the analysis report.

In some embodiments, upon receiving the data, the data processing function block 801 may decrypt the data by means of a decryption key. The decryption key may be sensing device specific and thus can only be used to decrypt data from a particular sensing device. The decrypted data may be further processed by the data processing function block 801. The data processing may comprise data smoothing by means of e.g., Savitzky-Golay smoothing and/or moving average. The Savitzky-Golay smoothing is a low-pass filtering technique which attenuates higher frequency noise while suppressing low-frequency noise derived from wearer motion. This is a Finite Impulse Response (FIR) filter meaning its impulse response is of finite duration.

In some embodiments, the data processing may further comprise subtracting the data originated from the accelerometer 301(*b*) from the data originated from the multi-channel pulse oximeter 301(*a*) so as to remove or minimise the motion induced data interference. Following that, the data processing function block 801 may perform recompiling of pulsatile coordinate data points so as to generate a corresponding full heart rhythm waveform, similar to the waveform shown in FIG. 1. The generated high fidelity heart rhythm waveform may then be stored in a directory created in the data base 803 that is dedicated for storing the information of the wearer.

In some embodiments and with reference to FIG. 9, the deterministic analysis performed by the data analysis function block 802 may comprise three main steps: step 901, identifying features indicative of heart rhythm anomalies on the generated pulse oximetry-derived heart rhythm waveform; step 902, assigning evidence scores to the identified features; step 903, calculating an overall evidence score based on the previously assigned evidence scores; step 904, determining presence of heart arrhythmia based on the overall evidence score. In different embodiments, the identification of features indicative of heart rhythm anomalies performed at step 901 may be based on the generated pulse oximetry-derived heart rhythm waveform and ECG data (e.g., the data transmitted from the sensing device to the remote server during the last continuous long-term recording).

Specifically, when used to determine the presence of AFib, the deterministic analysis may be carried out in a way described below.

At step 901, the high fidelity heart rhythm waveform may be used for computation of systolic peak (R-wave 130), calculation of peak-to-peak intervals, interpolation of peak-to-peak times over a number of measured heart cycles to establish variance, and computational identification of the presence of features which may be indicative of a P-wave. The computation of systolic peak may be achieved via e.g., calculation of the positive-to-negative slope change on signals with an amplitude >75% of the maxima of all measured samples to that point (repeats for each waveform). The calculation of peak-to-peak intervals may be achieved via e.g., subtraction of the time measurements between the most recently identified R-wave 130 peak and the previously measured peak. The variance may be compared to an established acceptable range in order to identify anomalous variance. The computational identification of the presence of features may be achieved via e.g., negative-to-positive and positive-to-negative slope calculations on a set number of data points preceding identified systolic peaks;

At step 902, based on the calculation results obtained at step 901, flaggable anomalies of the heart rhythm waveform may be determined and an AFib evidence score may be assigned to each of them. The flaggable anomalies may comprise for example absence of features which may be indicative of a P-wave 110, and R-wave 130 variation outside of a predefined nominal range.

At step 903, the flagged data may be further processed for false-positive reduction. This may be achieved via e.g., analysis of flagged areas via derivative threshold algorithm analysed by a machine learning (ML) model such as support vector machine model (SVM). An SVM is a supervised learning model designed to be utilised with learning algorithms which examine data for classification and regression analysis, resulting in waveform features being detected with greater reliability. Analytical methods within this ML algorithm may comprise for example time-frequency examination, singular value decomposition, empirical mode decomposition, sparse signal recovery, and spectrum analysis for spectral-peak tracking. These methods may aid in obtaining usable data in the case that motion-induced interference is still present. The ML algorithm is essentially searching for sequences of R-R irregularity and patterns which indicate the presence or absence of P-waves 110, both of which are deduced as present or absent via the calculation of evidence scores. The strength of these evidence scores stems from data training sets that the ML algorithm has learned from. The post-processing flagged data may then be used for recalculation of AFib evidence scores and further training of the ML model.

At step 904, the final AFib evidence scores may be used to determine the presence of AFib and the relevant analysis data may be used for compiling of a final report. The report may be for example in PDF format in which a red box may be drawn around the sectioned anomalous waveforms, and a timestamped notification, link, and explanation for the flagged anomaly may be shown.

In an embodiment, the system of FIG. 2 may be used to provide an end-to-end service for the diagnosis of AFib and other heart rhythm abnormalities. The end-to-end service may comprise for example the following three phases.

Phase 1: Clinician-Initiated Device Provisioning

After a patient presents to a clinician with suspected heart rhythm abnormality, the clinician opens a browser-based referral portal (or the online analysis platform 204) and enters the patient's details. A patient directory is automatically created in the online portal upon clinician referral. The supplier or distributor of the sensing devices is notified of the referral, which is accepted by selecting the newly created directory and clicking 'link device'. The online portal detects a technician removing a sensing 201 device up from a charging device 202, pairing the patient directory with that specific sensing device 201 automatically (in a similar fashion to how a computer detects the removal of a USB device). A decryption key is generated upon the directory association, used to decrypt data uploaded at the end of the collection period. The sensing device 201 is placed in a package along with other accessories, such as body attachment means (e.g. straps, bands (wristbands/armbands)) and user manual.

Phase 2: Patient Monitoring

Upon receiving the sensing device 201, the patient attaches the sensing device 201 to their body. The sensing device 201 can be worn continuously for the duration of monitoring (up to 90 days). The sensing device 201 automatically begins data recording after a satisfactory heartbeat signal is detected. By the time a prescribed monitoring period has passed, the patient returns the sensing device 201 to the supplier.

Phase 3: Data Collection and Analysis

Upon receiving the sensing device 202, the technician places the sensing device 201 into a charge device 202 and enables data uploading to the online portal. The uploaded data is decrypted with the unique decryption key and subsequently processed in a desired manner. An analysis report is generated after a deterministic analysis, e.g., the analysis process shown in FIG. 10, is performed on the processed data. The analysis report containing the information as to whether or not heart rhythm abnormalities are present is sent to the clinician for review.

In a different embodiment, any person may be able to buy a sensing device 201 along with a charging device 202 and other accessories (e.g., a wristband or an armband and a manual) from a local store or an online store. Upon receiving the sensing device, the person may register a user account on the online analysis platform 204 and create a personal profile by providing relevant personal information. Following the creation of the personal profile, the person may wear the sensing device and start recording his/her heart rhythm data. After a recommended recording period is over or the battery is discharged (e.g., 90 days), the sensing device 201 may be placed into the charging device 202 which is connected to a personal computer 203. The physical connection between the sensing device 201 and the charging device 202 may enable charging of the sensing device 201 as well as uploading the recorded data to the online analysis platform 204 either via a dedicated software application or a web browser. The online analysis platform 204 may perform deterministic analysis as shown in FIG. 9 and may provide the person with an evaluation result as to whether or not heart rhythm abnormalities (e.g., AFib) are detected during the last recording period. Relevant heart rhythm data may also be shown in order to support the finding/evaluation. The person may then send the evaluation result and the supporting data to a medical doctor (e.g., general practitioner (GP)) who will decide if a referral for specialist treatment is needed, for example.

Further embodiments are disclosed in the subsequent numbered list of clauses:

1. A wearable device for heart rhythm monitoring, comprising: a sensor unit comprising at least one pulse oximeter;
- a processor unit;
- a memory unit;
- a power unit comprising a battery;
- wherein, the at least one pulse oximeter is configured to measure optically a bloodstream at a sampling rate and output measured data;
- wherein, the processor unit is configured to process the measured data and determine a time for the processed data to be automatically recorded in the memory unit;
- wherein, the processor unit is configured to dynamically adjust the sampling rate of the at least one pulse oximeter based on a predetermined event.

2. A wearable device for heart rhythm monitoring as defined in clause 1, wherein the predetermined event is one or more of: a battery charge level of the wearable device, a detected physical activity level, and quality of one or more detected sensor signals.

3. A wearable device for heart rhythm monitoring as defined in clause 2, wherein the dynamic adjustment of the sampling rate of the at least one pulse oximeter is such that the sampling rate is reduced as the battery charge level of the wearable device drops.

4. A wearable device for heart rhythm monitoring as defined in clauses 2 to 3, wherein the sensor unit further comprises a tri-axis accelerometer configured to track motion of the wearable device at the same sampling rate as that of the at least one pulse oximeter.

5. A wearable device for heart rhythm monitoring as defined in clause 4, wherein the processor unit is configured to further dynamically adjust the sampling rate of the at least one pulse oximeter and the tri-axis accelerometer based on the tracked motion of the wearable device.

6. A wearable device for heart rhythm monitoring as defined in clause 5, wherein the further dynamic adjustment of the sampling rate is such that the sampling rate is increased as the tracked motion intensifies.

7. A wearable device for heart rhythm monitoring as defined in any preceding clause, wherein the sampling rate is adjustable in a range approximately between 215 Hz and 1000 Hz.

8. A wearable device for heart rhythm monitoring as defined in any preceding clause, wherein the processing of the measured data comprises application of interpolation to the measured data such that the number of sampling data points is maintained even when the sampling rate is dynamically adjusted.

9. A wearable device for heart rhythm monitoring as defined in any preceding clause, wherein the time for the automatic recording of the processed data is determined by evaluating an initial heartbeat signal.

10. A wearable device for heart rhythm monitoring as defined in clause 9, wherein the evaluation of the initial heartbeat signal comprises matching the initial heartbeat signal to a predefined heartbeat signal.

11. A wearable device for heart rhythm monitoring as defined in any preceding clause, wherein the processing of the measured data comprises noise reduction and encryption.

12. A wearable device for heart rhythm monitoring as defined in any preceding clause, wherein the capacity level of the battery is equivalent to or greater than 1400 mAh.

13. A wearable device for heart rhythm monitoring as defined in clause 12, wherein the battery is operable to enable a maximum duration of 90 days for a single continuous recording of the processed data.

14. A wearable device for heart rhythm monitoring as defined in any preceding clause, wherein the at least one pulse oximeter emits at least two wavelengths of 660 nm and 940 nm.

15. A wearable device for heart rhythm monitoring as defined in clause 14, wherein the at least two wavelengths of 660 nm and 940 nm further comprises one or more other wavelengths between 400 and 970 nm.

16. A wearable device for heart rhythm monitoring as defined in any preceding clause, further comprising an external casing configured to enclose at least the sensor unit, the processor unit, the power unit and the memory unit.

17. A wearable device for heart rhythm monitoring as defined in clause 16, wherein at least a bottom part of the external casing is made of a polyurethane gel elastomer.

18. A wearable device for heart rhythm monitoring as defined in clauses 16 or 17, wherein the external casing further comprises a first set of metal contact points, each metal contact point being connected to one contact of a first data transfer and charging circuitry.

19. A charging device configured for charging and transferring data from a wearable device as defined in clauses 1 to 18, comprising:
- an AC-DC Converter configured to convert the mains AC supply to DC power;
- a data transfer and charging unit comprising a second data transfer and charging circuitry; and
- at least one charging bay recessed from a top surface of the charging device and configured to accommodate the wearable device;
- wherein, the at least one charging bay comprises a second set of metal contact points configured to establish complementary connections to the wearable device, further wherein each metal contact point is connected to one contact of the second data transfer and charging circuitry.

20. A charging device as defined in clause 19, wherein, upon complementary connections being established with the wearable device, the data transfer and charging unit is configured to enable charging of the wearable device and data communication between the wearable device and a computing device.

21. A system for detecting heart rhythm abnormalities, comprising a wearable device comprising at least one pulse oximeter and configured to measure a bloodstream at a sampling rate and record electrical signal data;

a charging device configured for charging the wearable device and enabling data transferring therefrom;

a computing device in connection with both the charging device and a data network; and an online analysis platform accessible by the computer device and configured to process and analyse electrical signal data transferred from the wearable device in order to determine heart rhythm abnormalities;

wherein upon detecting a satisfactory heartbeat signal, the wearable device automatically begins recording of electrical signal data;

wherein the wearable device is operable to dynamically adjust the sampling rate based on a predetermined event.

22. A system for detecting a heart rhythm abnormality as defined in clause 21, wherein the predetermined event is one or more of: a battery charge level of the wearable device, a detected physical activity level, and quality of one or more detected sensor signals.

23. A system for detecting a heart rhythm abnormality as defined in clause 22, wherein the wearable device is operable to reduce the sampling rate as the battery charge level drops.

24. A system for detecting a heart rhythm abnormality as defined in any of clauses 21 to 23, wherein the recording of the electrical signal data lasts a maximum duration of 90 days.

25. A system for detecting a heart rhythm abnormality as defined in any of clauses 21 to 24, wherein the heartbeat signal is satisfactory if such heartbeat signal matches to a predefined heartbeat signal.

26. A system for detecting a heart rhythm abnormality as defined in any of clauses 21 to 25, wherein the online analysis platform is accessible by the computing device via a web browser or a software application.

27. A system for detecting a heart rhythm abnormality as defined in any of clauses 21 to 26, wherein the processing of the electrical signal data comprises decryption of the electrical signal data with a decryption key.

28. A system for detecting a heart rhythm abnormality as defined in any of clauses 21 to 27, wherein the processing of the electrical signal data further comprises application of interpolation to the measured data such that the number of sampling data points is maintained even when the sampling rate is dynamically adjusted 29. A system for detecting a heart rhythm abnormality as defined in clause 28, wherein the processing of the electrical signal data further comprises noise reduction of the electrical signal data.

30. A system for detecting a heart rhythm abnormality as defined in clause 29, wherein the wearable device further comprises a tri-axis accelerometer configured to track motion of the device at the same sampling rate of the at least one pulse oximeter and generate motion data.

31. A system for detecting a heart rhythm abnormality as defined in clause 30, wherein the noise reduction of the electrical signal data is obtained by subtracting the motion data from the electrical signal data.

32. A system for detecting a heart rhythm abnormality as defined in any of clauses 30 or 31, wherein the motion data is configured to determine the detected physical activity level for dynamically adjusting the sampling rate.

33. A system for detecting a heart rhythm abnormality as defined in any of clauses 29 to 32, wherein the online analysis platform is configured to reconstruct a heart rhythm waveform based on the processed electrical signal data.

34. A system for detecting a heart rhythm abnormality as defined in clause 33, wherein the online analysis platform is configured to identify at least one feature indicative of heart rhythm anomalies on the reconstructed heart rhythm waveform.

35. A system for detecting a heart rhythm abnormality as defined in clause 34, wherein the at least one feature indicative of heart rhythm anomalies comprises one or both of: absence of P-wave and variance of peak-to-peak intervals of R-waves exceeding a predefined variance range.

36. A system for detecting a heart rhythm abnormality as defined in any of clauses 34 or 34, wherein the online analysis platform is configured to assign evidence scores to the identified at least one feature.

37. A system for detecting a heart rhythm abnormality as defined in clause 36, wherein the online analysis platform is configured to calculate an overall evidence score based on the assigned evidence scores.

38. A system for detecting a heart rhythm abnormality as defined in clause 37, wherein the online analysis platform is configured to determine presence of a heart rhythm abnormality based on the overall evidence score.

39. A system for detecting a heart rhythm abnormality as defined in clause 38, wherein the heart rhythm abnormality comprises atrial fibrillation (AFib).

40. A system for detecting a heart rhythm abnormality as defined in any of clauses 38 or 39, wherein the online analysis platform is operable to store the analysis report in a dedicated directory on the online analysis platform.

41. A system for detecting a heart rhythm abnormality as defined in clause 40, wherein the dedicated directory is associated with the wearable device and the decryption key.

42. A system for detecting a heart rhythm abnormality as defined in any of clauses 21 to 41, wherein the sampling rate is adjustable in a range approximately between 215 Hz and 1000 Hz.

43. A method for heart rhythm monitoring, comprising:

measuring optically a bloodstream optically at a sampling rate and outputting measured data using at least one pulse oximeter;

processing the measured data and determining a time for the processed data to be automatically recorded using a processor unit;

adjusting dynamically the sampling rate of the at least one pulse oximeter based on a predetermined event.

44. A method for heart rhythm monitoring as defined in clause 43, wherein the predetermined event is one or more of: a battery charge level of the wearable device, a detected physical activity level, and quality of one or more detected sensor signals.

45. A method for determining a heart rhythm abnormality, comprising: recording a electrical signal data by measuring at a sampling rate with a wearable device comprising at least one pulse oximeter;

transferring the data from the at least one pulse oximeter based wearable device to an online analysis platform;

processing the electrical signal data to reconstruct a heart rhythm waveform; identifying at least one feature indicative of heart rhythm anomalies on the reconstructed heart rhythm waveform;

assigning evidence scores to the identified at least one feature;

calculating an overall evidence score based on the assigned evidence scores; and determining presence of a heart rhythm abnormality based on the overall evidence score;

wherein the wearable device is operable to dynamically adjust the sampling rate based on one or more of: a battery charge level of the wearable device, a detected physical activity level, and quality of one or more detected sensor signal.

46. A method for determining a heart rhythm abnormality as defined in clause 45, the sampling rate is adjustable in a range approximately between 215 Hz and 1000 Hz.

It will be appreciated that the above described embodiments are given by way of example only, and that various modifications may be made to the embodiments without departing from the scope of the invention as defined in the appended claims.

The invention claimed is:

1. A wearable device for long-term monitoring of heart rhythm waveforms, comprising:

a sensor unit comprising at least one pulse oximeter and an ECG sensor having at least one pair of dry electrodes configured to be in contact with a body surface;

a processor unit;

a memory unit; and a power unit comprising a battery and configured to disseminate battery power amongst various components of the wearable device;

wherein, the at least one pulse oximeter is configured to measure optically a bloodstream at a sampling rate and output first oximetry data;

wherein, the processor unit is configured to process the first oximetry data and determine a time to automatically start a single continuous recording of the processed first oximetry data in the memory unit;

wherein, the processor unit is configured to dynamically adjust the sampling rate of the at least one pulse oximeter based on a predetermined event, wherein the ECG sensor is configured to measure one or more voltage signals in relation to heart rhythm activity, each voltage signal being measured across one pair of electrodes, and output second ECG data comprising the one or more voltage signals, wherein the time for the automatic recording of the processed first oximetry data is determined when one or more voltage signals of the ECG sensor exceed a voltage threshold, wherein the processor unit is configured to analyze the processed first oximetry data to determine whether there is any irregularity in peak-to-peak pulse timings, and wherein, during a primary, power-conserving monitoring mode, the ECG sensor is maintained in a dormant state while when an irregularity in peak-to-peak pulse timings is determined from the first oximetry data, the processor unit is configured to automatically transition the ECG sensor from the dormant state to an active state and record the second ECG data in the memory unit.

2. The wearable device as claimed in claim 1, wherein the predetermined event is one or more of: a battery charge level of the wearable device, a detected physical activity level, and quality of one or more detected sensor signals.

3. The wearable device as claimed in claim 2, wherein the dynamic adjustment of the sampling rate of the at least one pulse oximeter is such that the sampling rate is reduced as the battery charge level of the wearable device drops.

4. The wearable device as claimed in claim 2, wherein the sensor unit further comprises a tri-axis accelerometer configured to track motion of the wearable device at the same sampling rate as that of the at least one pulse oximeter, the tracked motion being used to determine the detected physical activity level.

5. The wearable device as claimed in claim 4, wherein the further dynamic adjustment of the sampling rate is such that the sampling rate is increased as the tracked motion intensifies.

6. The wearable device as claimed in claim 1, wherein the sampling rate is adjustable in a range approximately between 215 Hz and 1000 Hz.

7. The wearable device as claimed in claim 1, wherein the processor unit is configured to end the recording of the second ECG data when any of the following two conditions is met:

1) A fixed duration of recording time is reached; or 2) no irregularity in peak-to-peak pulse timings is determined in a most recent duration of time.

8. The wearable device as claimed in claim 1, wherein upon ending of the recording of the second ECG data, the processor unit is configured to analyze the second ECG data so as to select ECG data with the best signal to noise ratio.

9. The wearable device as claimed in claim 1, further comprising a cellular module wherein the processor unit is configured to activate the cellular module so as to transmit the selected ECG data to a remote server via a mobile network without affecting the recording of the first oximetry data.

10. A method for long-term monitoring of heart rhythm waveforms, comprising:

measuring optically a bloodstream at a sampling rate and outputting first oximetry data using at least one pulse oximeter;

maintaining an ECG sensor in an active, power-conserving state;

adjusting dynamically the sampling rate of the at least one pulse oximeter based on a predetermined event;

recording automatically, from a first time instance, the first oximetry data measured by the at least one pulse oximeter;

analyzing the first oximetry data to determine presence of any irregularity in peak-to-peak pulse timings;

upon identifying an irregularity in peak-to-peak pulse timings, automatically activating the ECG sensor to measure heart rhythm activity using one or more pairs of dry electrodes;

recording automatically, from a second time instance, second ECG data comprising one or more voltage signals; and transmitting at least part of the second ECG data via a mobile network without affecting the recording of the first oximetry data;

wherein the first time instance is when one or more voltage signals generated by the ECG sensor exceeds a voltage threshold; and wherein the second time instance is when irregularity in peak-to-peak pulse timings is identified in the first oximetry data.

11. A non-transient computer program carrier comprising a computer program comprising program instructions to perform the method comprising:

measuring optically a bloodstream at a sampling rate and outputting oximetry data using at least one pulse oximeter;

maintaining an ECG sensor in an active, power-conserving state;

adjusting dynamically the sampling rate of the at least one pulse oximeter based on a predetermined event;

recording automatically, from a first time instance, the first oximetry data measured by the at least one pulse oximeter;

analyzing the first oximetry data to determine presence of any irregularity in peak-to-peak pulse timings;

upon identifying an irregularity in peak-to-peak pulse timings, automatically activating the ECG sensor to measure heart rhythm activity using one or more pairs of dry electrodes;

recording automatically, from a second time instance, second ECG data comprising one or more voltage signals; and transmitting at least part of the second ECG data via a mobile network without affecting the recording of the first oximetry data, wherein the first time instance is when one or more voltage signals generated by the ECG sensor exceeds a voltage threshold, and wherein the second time instance is when irregularity in peak-to-peak pulse timings is identified in the first oximetry data, when run on a suitable apparatus comprising a processor unit.

* * * * *